*(12)* United States Patent
Sako et al.

(10) Patent No.: US 12,336,828 B2
(45) Date of Patent: Jun. 24, 2025

(54) BIOLOGICAL INFORMATION MEASUREMENT DEVICE, METHOD FOR CONTROLLING BIOLOGICAL INFORMATION MEASUREMENT DEVICE, AND PROGRAM

(71) Applicant: OMRON HEALTHCARE Co., Ltd., Kyoto (JP)

(72) Inventors: Natsuki Sako, Kyoto (JP); Shinya Kodaka, Kyoto (JP); Miho Hiraki, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 523 days.

(21) Appl. No.: 17/931,372

(22) Filed: Sep. 12, 2022

(65) Prior Publication Data

US 2023/0000417 A1  Jan. 5, 2023

Related U.S. Application Data

(63) Continuation of application No. PCT/JP2021/008558, filed on Mar. 4, 2021.

(30) Foreign Application Priority Data

Mar. 17, 2020  (JP) ................... 2020-046034

(51) Int. Cl.
*A61B 5/329*  (2021.01)
*A61B 5/0205*  (2006.01)

(52) U.S. Cl.
CPC ............ *A61B 5/329* (2021.01); *A61B 5/0205* (2013.01)

(58) Field of Classification Search
None
See application file for complete search history.

(56) References Cited

U.S. PATENT DOCUMENTS

2014/0088394 A1* 3/2014 Sunderland ............ A61B 5/254
600/373
2016/0374577 A1* 12/2016 Baxi ...................... A61B 5/369
600/382

(Continued)

FOREIGN PATENT DOCUMENTS

JP  5-293091 A  11/1993
JP  2008-237379 A  10/2008
JP  2009-28153 A  2/2009

OTHER PUBLICATIONS

International Search Report (ISR) for International Application No. PCT/JP2021/008558, dated Apr. 20, 2021.

(Continued)

*Primary Examiner* — James M Kish
*Assistant Examiner* — James Moss
(74) *Attorney, Agent, or Firm* — Birch, Stewart, Kolasch & Birch, LLP

(57) ABSTRACT

A biological information measurement device, including an electrode contact state detector including a first contact detection circuit connected to either the first electrode or the second electrode among the electrodes, a second contact detection circuit connected to the third electrode, and a contact state determinator for determining a contact state indicating which of the electrodes is in contact with a surface of the measurement target based on a first signal output from the first contact detection circuit and a second signal output from the second contact detection circuit, and an input receiver for receiving a contact of the electrode with respect to the surface of the measurement target as input of predetermined operation associated with the contact state.

16 Claims, 14 Drawing Sheets

(56) References Cited

U.S. PATENT DOCUMENTS

2016/0378965 A1    12/2016  Choe et al.
2021/0169420 A1*    6/2021  Jung ................... A61B 5/7475
2022/0346718 A1*   11/2022  Ono ........................ A61B 5/28

OTHER PUBLICATIONS

International Preliminary Report on Patentability for International Application No. PCT/JP2021/008558, dated Dec. 7, 2021.

* cited by examiner

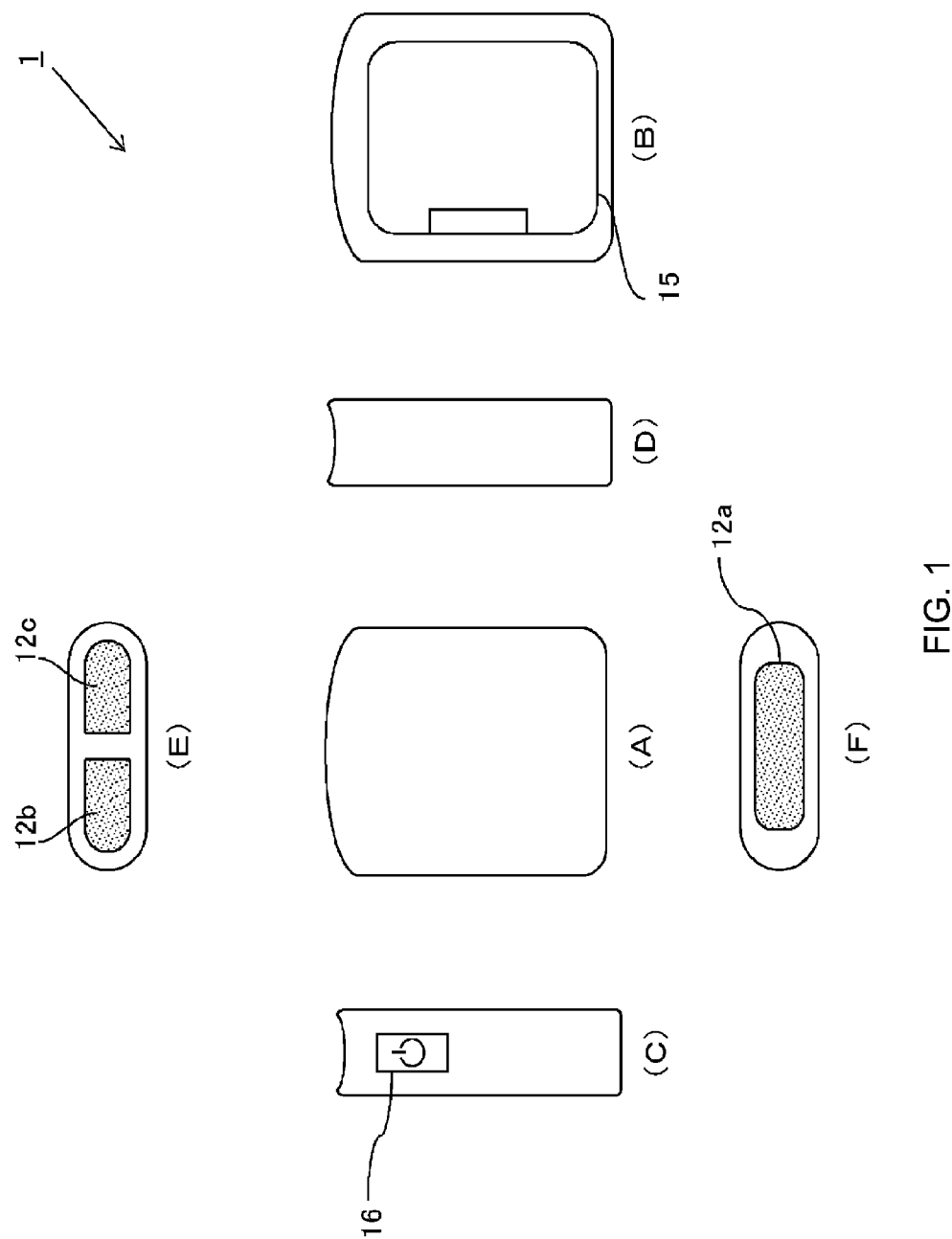

| RED | CHEST PAIN |
|---|---|
| PURPLE | DIZZINESS |
| ORANGE | MALAISE |
| YELLOW | NAUSEA |
| GREEN | PALPITATION |
| LIGHT BRUE | SHORTNESS OF BREATH |
| BLUE | SYNCOPE |
| TURN OFF | OTHER |

RED: WHEN PHYSICAL CONDITION IS INPUT

| RED | LARGE |
|---|---|
| YELLOW | NORMAL |
| GREEN | SMALL |
| BLUE | REST |

BLUE: WHEN EXERCISE LOAD IS INPUT

BIOLOGICAL INFORMATION MEASUREMENT DEVICE, METHOD FOR CONTROLLING BIOLOGICAL INFORMATION MEASUREMENT DEVICE, AND PROGRAM

CROSS-REFERENCE TO RELATED APPLICATIONS

This application is the U.S. national stage application filed pursuant to 35 U.S.C. 365(c) and 120 as a continuation of International Patent Application No. PCT/JP2021/008558, filed Mar. 4, 2021, which application claims priority to Japanese Patent Application No. 2020-046034, filed Mar. 17, 2020, which applications are incorporated herein by reference in their entireties.

TECHNICAL FIELD

The present invention belongs to the technical field related to healthcare, and particularly relates to a biological information measurement device, a method for controlling the biological information measurement device, and a non-transitory recording medium storing a program.

BACKGROUND ART

In recent years, it has become widespread to perform health management by: measuring information (hereinafter, also referred to as biological information) on the body and health of an individual such as a blood pressure value and an electrocardiographic waveform with a measurement device; and recording and analyzing the measurement result with an information terminal.

As an example of the measurement device as described above, a portable electrocardiographic measurement device for measuring an electrocardiographic waveform immediately when an abnormality occurs in everyday life (so-called event electrocardiographic testing), such as pain and palpitation in a chest, has been proposed, and a contribution to an early detection or appropriate treatment of heart disease is expected (for example, Patent Document 1).

Incidentally, when the measured electrocardiographic waveform is confirmed, there is a need to confirm only the electrocardiographic waveform measured at timing when the subject becomes aware of some symptom. In this regard, Patent Document 1 proposes a portable electrocardiographic measurement device that includes a liquid crystal display and an operation button, and is capable of inputting subjective symptoms of a subject and recording them together with the electrocardiographic waveform at the time of electrocardiographic measurement.

According to the electrocardiographic measurement device described in Patent Document 1, it is possible to efficiently confirm a biological waveform corresponding to a state of the subject at the time of measurement, such as an electrocardiographic waveform measured at the timing when the subject becomes aware of a certain symptom.

CITATION LIST—PATENT LITERATURE

Patent Document 1: JP 2009-28153 A

SUMMARY OF INVENTION

Technical Problem

However, in the technology described in Patent Document 1, a display device such as a liquid crystal display and an operation unit need to be provided, and thus the size of the measurement device is increased accordingly. This causes a problem that the holding of the device becomes unstable and the accuracy of the measurement is lowered when the measurement is performed. Also, in the first place, there is a problem in that the portability of the portable electrocardiographic measurement device is reduced.

In view of the problems described above, an object of the present invention is to provide a technology that enables input of predetermined information in a portable biological information measurement device including an electrode, and enables reduction in size by excluding an operation unit and a display screen for information input from a configuration of the device.

Solution to Problem

To solve the problem described above, the biological information measurement device according to the present invention includes a first electrode, a second electrode, and a third electrode, the biological information measurement device measuring biological information of a measurement target based on a potential difference between the first electrode and the third electrode. The biological information measurement device includes an electrode contact state detector including a first contact detection circuit connected to either the first electrode or the second electrode among the electrodes, a second contact detection circuit connected to the third electrode, and a contact state determinator configured to determine a contact state indicating which of the electrodes is in contact with a surface of the measurement target based on a first signal output from the first contact detection circuit and a second signal output from the second contact detection circuit, and an input receiver configured to receive a contact of the electrode with respect to the surface of the measurement target as input of predetermined operation associated with the contact state.

According to the configuration described above, by using the electrode for measuring biological information, it is possible to input an operation corresponding to each contact state to the device in accordance with a difference in the contact state of the electrode with the body (which electrode is in contact). Therefore, it is not necessary to separately provide an operation unit for inputting operation, and it is possible to input predetermined information to the device without increasing the size of the device.

Further, a contact detection electrode switcher configured to switch an electrode connected to the first contact detection circuit between the first electrode and the second electrode may be provided. Further, the contact detection electrode switcher may connect one of the first electrode and the second electrode, which is not connected to the first contact detection circuit, to a ground.

With such a configuration, even when input is performed using an electrode optimally arranged for measurement of biological information, the circuit of the electrode contact state detector for determining the input at the time of input of the operation can be switched so as to be connected to an electrode which is not inconvenient for performing the input operation, thereby improving convenience for the user.

Further, the contact state determinator may switch and execute, depending on the electrode connected to the first contact detection circuit, the determination of the contact state between a determination at time of measurement when the biological information of the measurement target is measured and a determination at time of operation input when the input of the predetermined operation is received, and the input receiver may receive a contact of each of the electrodes with respect to the surface of the measurement target as the input of the predetermined operation associated with the contact state when the contact state determinator is executing the determination at the time of operation input.

According to such a configuration, the contact determination of the electrode can be properly used depending on the case of performing the measurement of the biological information and the case of performing the input of the information, so that it is possible to prevent the input of the information from being erroneously performed at the time of the measurement of the biological information from occurring, and vice versa.

Further, the predetermined operation corresponding to the contact state may include selecting at least a predetermined item. With such a configuration, it is possible to make the input of the intended information related to the predetermined item only by intentionally changing the contact state of the electrode.

Further, the predetermined item may include a physical condition or an exercise load state when the biological information of the measurement target is measured. Here, the physical condition means a condition that a measurement target (hereinafter, also referred to as a user) becomes aware at the time of measurement of biological information, and may include items such as chest pain, dizziness, malaise, nausea, palpitations, shortness of breath, syncope, and no abnormality. The exercise load state means an amount of exercise perceived by the user at the time of measurement of biological information, and may include, for example, large, normal, small, and rest.

By associating the physical condition or the exercise load state at the time of measurement of the biological information with the measurement data as described above, it is possible to contribute to efficient confirmation of the measurement data, improvement in analysis accuracy of the measurement data, and the like.

Further, the biological information measurement device may further include a notifier, and the notifier may be configured to notify information related to measurement of the biological information when the biological information of the measurement target is measured, and notify information related to a content of the predetermined item when the input of the predetermined operation is received. When the notifier is provided, it is possible to notify various types of information, and the convenience of the user can be improved. In addition, when a component such as an LED that does not occupy a large space is used as the notifier, it is also possible to minimize the adverse effect of an increase in the device size. Note that the notifier is not limited to the LED, but may be a liquid crystal display, a speaker, or the like.

Further, the biological information may be an electrocardiographic waveform. The present invention is suitable for such a device.

Additionally, a method for controlling a biological information measurement device according to the present invention is a method for controlling a biological information measurement device including a first electrode, a second electrode, and a third electrode, the biological information measurement device measuring biological information of a measurement target based on a potential difference between the first electrode and the third electrode, the method including a measurement step of measuring the biological information of the measurement target, and an input reception step of receiving input of predetermined operation. In the input reception step, a contact state of each of the electrodes with respect to a surface of the measurement target is determined, and in accordance with a result of the determination, a contact of each of the electrodes with respect to the surface of the measurement target is received as input of predetermined operation associated with the contact state.

In addition, the present invention can be considered as a program for causing the biological information measurement device to execute the above-described method, and a computer-readable recording medium including such a program recorded therein in a non-transitory manner.

Also, the configurations and processing described above can be combined with one another to constitute the present invention unless the combination leads to contradiction.

Advantageous Effects of Invention

According to the present invention, it is possible to provide a technology that enables input of predetermined information in a portable biological information measurement device including an electrode, and enables reduction in size by excluding an operation unit and a display screen for information input from a configuration of the device.

BRIEF DESCRIPTION OF DRAWINGS

Various embodiments are disclosed, by way of example only, with reference to the accompanying schematic drawings in which corresponding reference symbols indicate corresponding parts, in which:

FIG. 1 is a six-sided view illustrating a configuration of a portable electrocardiograph according to a first embodiment. (A) of FIG. 1 is a front view illustrating the configuration of the portable electrocardiograph according to the first embodiment. (B) of FIG. 1 is a rear view illustrating the configuration of the portable electrocardiograph according to the first embodiment. (C) of FIG. 1 is a left side view illustrating the configuration of the portable electrocardiograph according to the first embodiment. (D) of FIG. 1 is a right side view illustrating the configuration of the portable electrocardiograph according to the first embodiment. (E) of FIG. 1 is a plan view illustrating the configuration of the portable electrocardiograph according to the first embodiment. (F) of FIG. 1 is a bottom view illustrating the configuration of the portable electrocardiograph according to the first embodiment;

DESCRIPTION OF EMBODIMENTS

First Embodiment

Figure 2A:
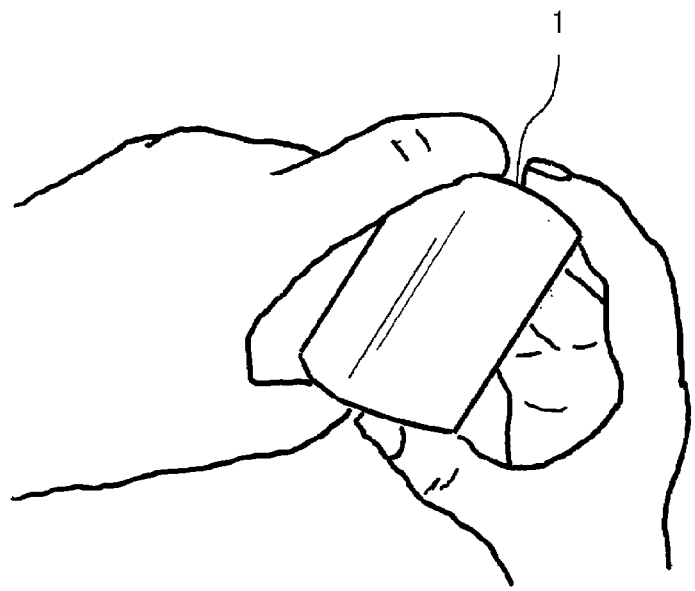
FIG. 2(A) is a first explanatory diagram illustrating an example of a method of holding the device when input is performed by an electrode of the portable electrocardiograph according to the first embodiment.

Embodiments of the present invention will be specifically described below with reference to the drawings. It should be noted that the dimension, material, shape, relative arrangement and the like of the components described in the present embodiment are not intended to limit the scope of this invention to them alone, unless otherwise stated.

Device Configuration

FIG. 1 is a diagram illustrating a configuration of a portable electrocardiograph 1 according to the present embodiment. (A) of FIG. 1 is a front view illustrating the front of the body. Similarly, (B) of FIG. 1 is a rear view, (C) of FIG. 1 is a left side view, (D) of FIG. 1 is a right side view, (E) of FIG. 1 is a plan view, and (F) of FIG. 1 is a bottom view.

As illustrated in FIG. 1, a power switch 16 is provided on a left side surface of the portable electrocardiograph 1, and a battery housing opening and a battery cover 15 are arranged at the rear surface of the portable electrocardiograph 1.

Further, a bottom surface of the portable electrocardiograph 1 is provided with a left electrode 12a brought into contact with the left side of the body during electrocardiographic measurement. An upper surface side of the portable electrocardiograph 1, opposite to the bottom surface, is provided with a first right electrode 12b brought into contact with the center of the right-hand index finger and a second right electrode 12c brought into contact with the base of the right-hand index finger. The left electrode 12a in the present embodiment corresponds to a first electrode according to the present invention. Similarly, the first right electrode 12b corresponds to a second electrode, and the second right electrode 12c corresponds to a third electrode.

During electrocardiographic measurement, the portable electrocardiograph 1 is held by the right hand, and the right-hand index finger is placed on the upper surface portion of the portable electrocardiograph 1 in proper contact with the first right electrode 12b and the second right electrode 12c. The left electrode 12a is then brought into contact with a skin at a location corresponding to the desired measurement method. For example, in a case where measurement is performed by a so-called lead I, the left electrode 12a is brought into contact with the palm of the left hand. In a case where measurement is performed by a so-called lead V4, the left electrode 12a is brought into contact with the skin slightly leftward of the epigastric region of the left chest and below the nipple.

Figure 2B:
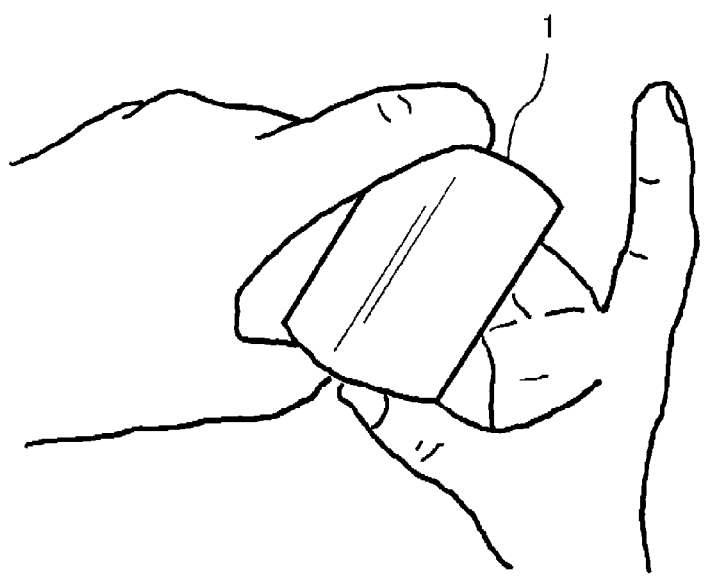
FIG. 2(B) is a second explanatory diagram illustrating an example of a method of holding the device when input is performed by an electrode of the portable electrocardiograph according to the first embodiment.

In addition, as will be described in detail later, input operation using an electrode can be performed in the portable electrocardiograph 1. When the input operation is performed, regardless of the electrode contact mode described above, it is sufficient if the portable electrocardiograph 1 is held in a mode in which the electrode is easily brought into contact for the input operation. FIG. 2 illustrates an example of a method for holding the portable electrocardiograph 1 when the input operation is performed. As illustrated in FIG. 2, for example, the input operation may be performed by bringing the left electrode 12a into contact with the right-hand thumb and/or the left-hand thumb, bringing the first right electrode 12b into contact with the left-hand index finger, and bringing the second right electrode 12c into contact with the right-hand index finger.

Figure 3:
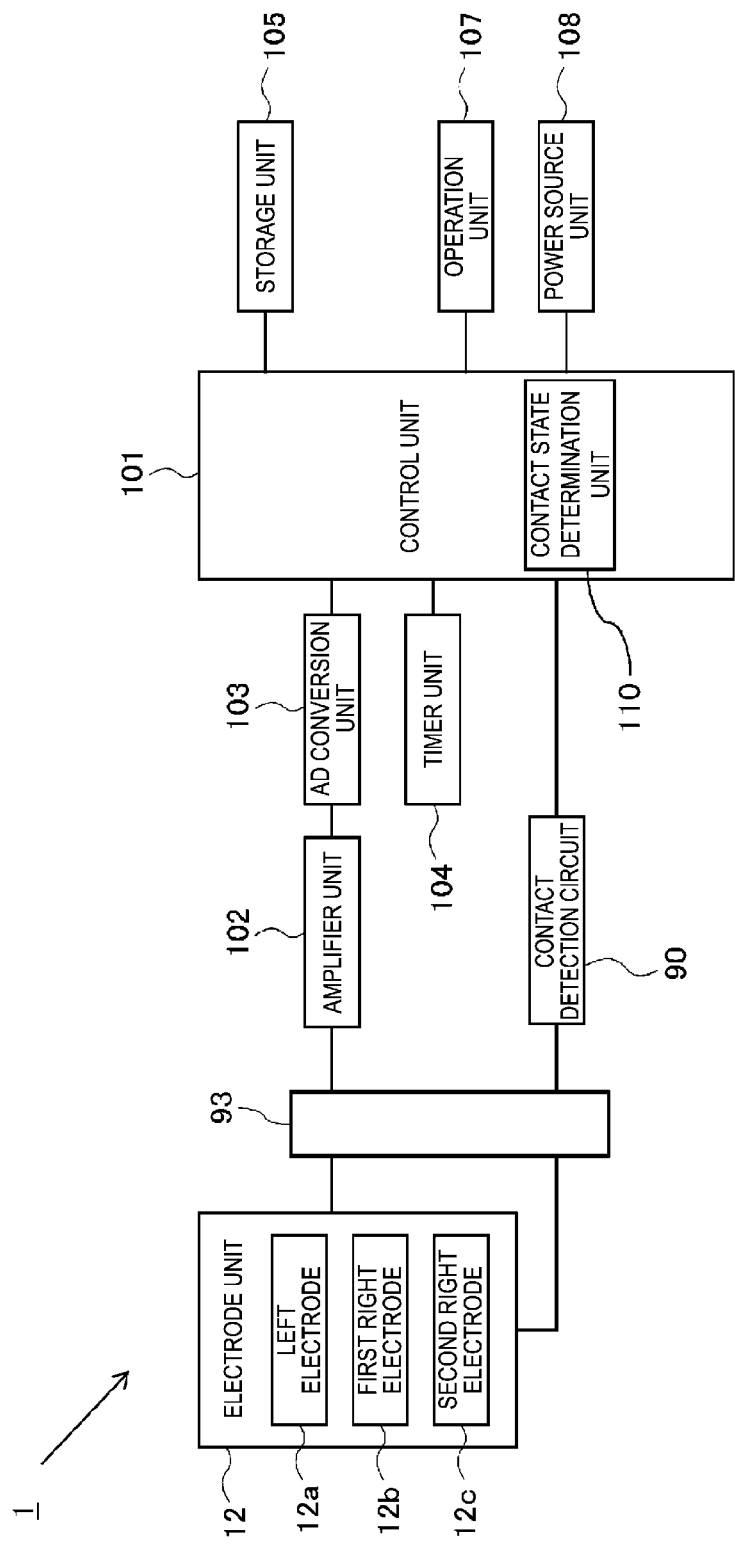
FIG. 3 is a block diagram illustrating a functional configuration of the portable electrocardiograph according to the first embodiment.

FIG. 3 illustrates a block diagram illustrating a functional configuration of the portable electrocardiograph 1. As illustrated in FIG. 3, the portable electrocardiograph 1 includes functional units including a control unit 101, an electrode unit 12, an amplifier unit 102, an AD conversion unit 103, a timer unit 104, a storage unit 105, an operation unit 107, a power source unit 108, a contact detection circuit 90, and a contact state determination unit 110.

The control unit 101 is a means for controlling the portable electrocardiograph 1, and includes a central processing unit (CPU) and the like, for example. In response to receiving operation of the user via the operation unit 107, the control unit 101 controls each component of the portable electrocardiograph 1 to execute various types of processing such as electrocardiographic measurement and operation input reception, in accordance with a predetermined program. Note that the predetermined program is stored in the storage unit 105 described below.

In addition, the control unit 101 includes, as a functional module, the contact state determination unit 110 that determines a contact state indicating which of the electrodes is in contact with the user based on an output signal from the contact detection circuit 90 described below. That is, the contact detection circuit 90 and the contact state determination unit 110 in the present embodiment correspond to an electrode contact state detector of the present invention.

The electrode unit 12 includes the left electrode 12a, the first right electrode 12b, and the second right electrode 12c, and functions as a sensor for detecting an electrocardiographic waveform, and also functions as the operation unit 107 as described later. The amplifier unit 102 has a function of amplifying a signal indicating an electrocardiographic waveform output from the electrode unit 12 as described later. The AD conversion unit 103 has functions of converting an analog signal amplified by the amplifier unit 102 into a digital signal and of transmitting the converted signal to the control unit 101.

The timer unit 104 has a function of measuring time with reference to the real time clock (RTC). For example, before the start of electrocardiographic measurement, a time during which all electrodes are in contact with the user, time from the start of measurement to the end of measurement, elapsed time after the end of measurement, and the like, are counted.

The storage unit 105 includes a main storage device such as a random access memory (RAM), and stores various types of information such as an application program, a measured electrocardiographic waveform, an electrocardiographic waveform analysis result, and a physical condition and an exercise load at the time of electrocardiographic measurement input by operation to be described later. In addition to the RAM, for example, a long-term storage medium such as a flash memory may be provided.

The operation unit 107 includes the power switch 16, the above-described electrode unit 12, and the like, and has a function of receiving the input operation from the user and causing the control unit 101 to execute processing according to the operation.

The power source unit 108 includes a battery that supplies the power required for operation of the device. The battery may be, for example, a secondary battery such as a lithium ion battery, or a primary battery.

Figure 4:
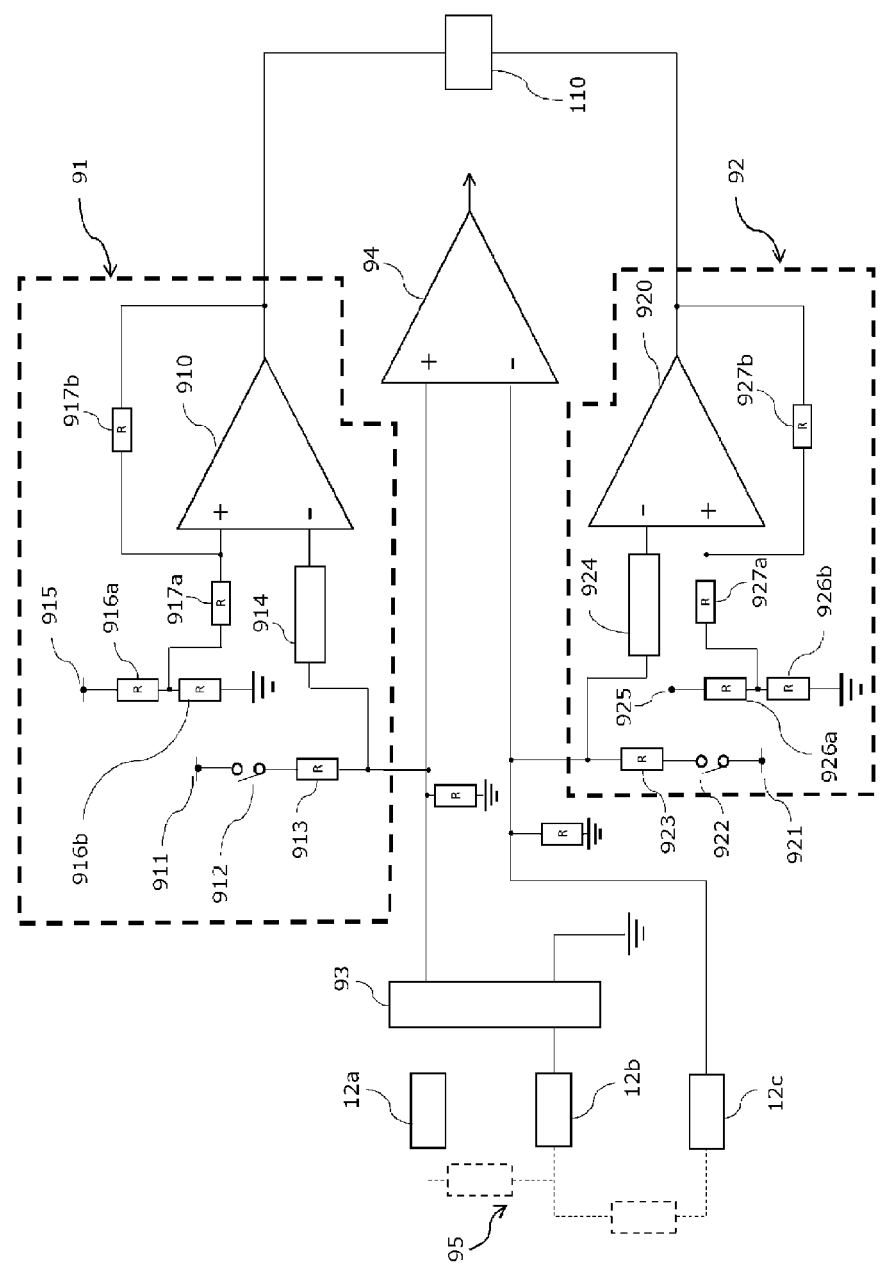
FIG. 4 is a circuit diagram illustrating a part of an electric circuit configuration of the portable electrocardiograph according to the first embodiment.

The contact detection circuit 90 is an electric circuit connected to each of the left electrode 12a, the first right electrode 12b, and the second right electrode 12c, and has a function of outputting whether or not these electrodes are in contact with the user. The contact detection circuit 90 is described in detail below on the basis of FIG. 4. FIG. 4 is a circuit diagram illustrating an electric circuit constituting the contact detection circuit 90.

The contact detection circuit 90 generally includes a first detection circuit 91 connected to the left electrode 12a or the first right electrode 12b and a second detection circuit 92 connected to the second right electrode 12c. The contact detection circuit 90 further includes a contact detection electrode switching unit 93 that switches the electrode connected to the first detection circuit 91 between the left electrode 12a and the first right electrode 12b under the control of the control unit 101.

Figure 5:
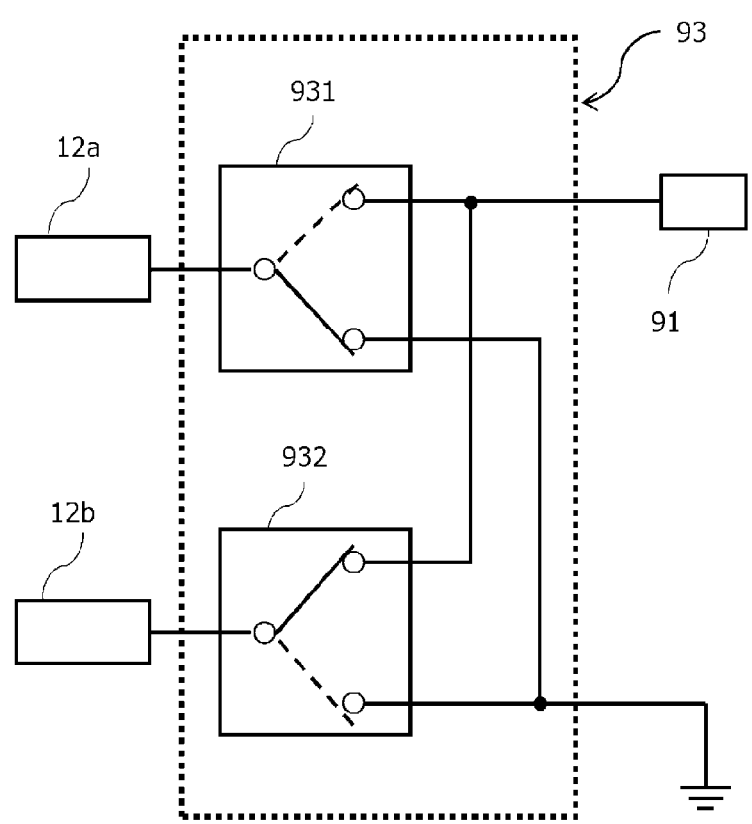
FIG. 5 is an explanatory diagram illustrating a configuration of a contact detection electrode switching unit of the portable electrocardiograph according to the first embodiment.

FIG. 5 illustrates the contact detection electrode switching unit 93. The contact detection electrode switching unit 93 includes a first selector (demultiplexer) 931 and a second selector 932, and switches the circuit to which the left electrode 12a and the first right electrode 12b are connected by switching the selectors 931, 932 under the control of the control unit 101.

In FIG. 4 and FIG. 5, when the left electrode 12a is connected to the first detection circuit 91, the first right electrode 12b is connected to the ground. Conversely, when the first right electrode 12b is connected to the first detection circuit 91, the left electrode 12a is connected to the ground. For example, at the time of electrocardiographic measurement, the left electrode 12a is connected to the first detection circuit 91 and the first right electrode 12b is connected to the ground as in the circuit connection example indicated by the broken line in each of the selectors 931, 932 illustrated in FIG. 5. On the other hand, at the time of the operation input to be described later, a connection destination of the left electrode 12a and the first right electrode 12b is switched as in the circuit connection example indicated by a solid line in each of the selectors 931, 932 illustrated in FIG. 5.

The first detection circuit 91 includes a first comparator 910, a first bias power source 911, a first switching element 912, a first pull-up resistor 913, a first RC filter 914, a first reference voltage power source 915, first reference voltage resistors 916a, 916b, and first hysteresis resistors 917a, 917b.

The first bias power source 911 applies a bias voltage (for example, about 3V) so that the electrode connected to the first detection circuit 91 has a bias potential higher than that of the electrode connected to the ground. The first switching element 912 is constituted by, for example, a field effect transistor (FET), and turns on/off the first bias power source 911 and the first pull-up resistor 913 under the control of the control unit 101. The first pull-up resistor 913 maintains the potential of the connected circuit at a high potential, and the first RC filter 914 removes a high-frequency component and inputs the voltage from the first bias power source 911 to the negative input terminal of the first comparator 910. Hereinafter, the potential input to the negative input terminal of the first comparator 910 is referred to as a first bias potential.

A predetermined contact detection reference voltage (for example, about 1.5 V) supplied from the first reference voltage power source 915 and adjusted by the first reference voltage resistors 916a, 916b is input to a positive input terminal of the first comparator 910. Hereinafter, the potential input to the positive input terminal of the first comparator 910 is referred to as a first detection reference potential.

The first comparator 910 is configured by, for example, an operational amplifier, and outputs a "High" signal when the first bias potential decreases by a predetermined hysteresis amount with respect to the first detection reference potential. On the other hand, when the first bias potential is equal to or higher than the first detection reference potential, a "Low" signal is output.

When both the left electrode 12a and the first right electrode 12b are simultaneously in contact with the user's skin surface, a current flows through the impedance of the human body to the first right electrode 12b having a lower potential than the left electrode 12a, a voltage drop occurs in the first pull-up resistor 913, and the first bias potential decreases. Thus, the output of the first comparator 910 changes from "Low" to "High". Note that a circuit 95 indicated by the broken line portion in the drawing indicates the path of the current via the impedance of the human body.

The second detection circuit 92 includes a second comparator 920, a second bias power source 921, a second switching element 922, a second pull-up resistor 923, a second RC filter 924, a second reference voltage power source 925, second reference voltage resistors 926a, 926b, and second hysteresis resistors 927a, 927b.

The second bias power source 921 applies a bias voltage to the second right electrode 12c so that the second right electrode 12c has a bias potential higher than that of the electrode connected to the ground. Other configurations and functions of the elements of the second detection circuit 92 are the same as those of the corresponding elements of the first detection circuit 91, and thus detailed description thereof will be omitted.

The output signal of the first comparator 910 and the second comparator 920 is sent to the CPU (control unit 101), and the contact state determination unit 110 determines whether any electrode is in contact with the body. The contact state determination unit 110 determines that all the electrodes are in contact with the body, for example, if the output of each comparator is "High".

As illustrated in FIG. 4 and FIG. 5, either the left electrode 12a or the first right electrode 12b is connected to the positive input terminal of a differential amplifier 94, and the second right electrode 12c is connected to the negative input terminal of the differential amplifier 94. In addition, an electrode of the left electrode 12a or the first right electrode 12b, which is not connected to the positive input terminal of the differential amplifier 94, is connected to the ground. For example, at the time of electrocardiographic measurement, the left electrode 12a is connected to the positive input terminal of the differential amplifier 94, and the differential amplifier 94 amplifies and outputs the potential difference between the left electrode 12a and the second right electrode 12c, and the output is transmitted via a filter circuit (not illustrated) to the amplifier unit 102 and the AD conversion unit 103, whereby the electrocardiographic measurement is performed.

Flow of Processing by Portable Electrocardiograph

Figure 6:
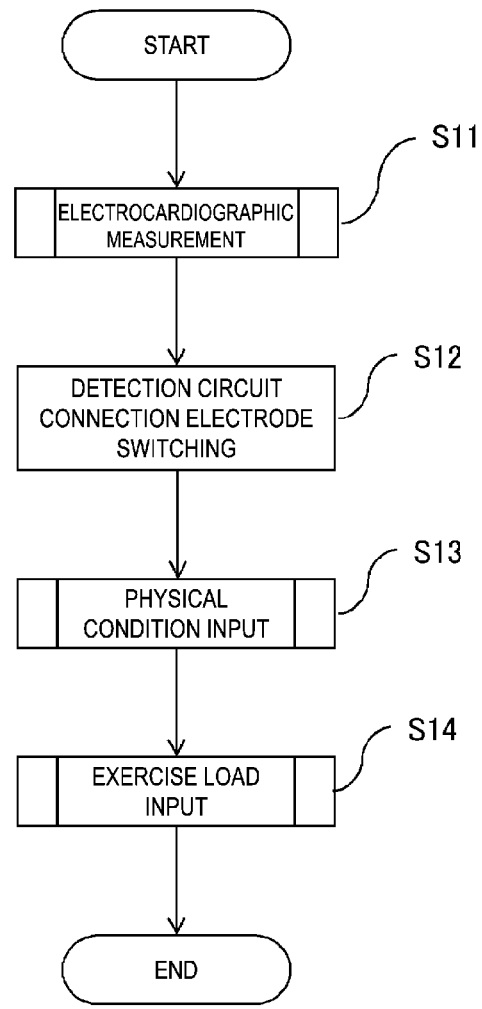
FIG. 6 is a flowchart illustrating a procedure of processing when electrocardiographic measurement is performed using the portable electrocardiograph according to the first embodiment.

Now, based on FIG. 6 to FIG. 10, a description will be given for operation of the portable electrocardiograph 1 when the electrocardiographic measurement is performed. FIG. 6 is a flowchart illustrating a procedure of processing when the electrocardiographic measurement is performed using the portable electrocardiograph 1. Further, FIG. 7 is a flowchart illustrating a subroutine at the time of electrocardiographic waveform measurement, and FIG. 8 is a flowchart illustrating a subroutine related to electrode contact detection processing before the electrocardiographic waveform measurement.

As illustrated in FIG. 6, when the electrocardiographic measurement is performed with the portable electrocardiograph 1 according to the present embodiment, after performing the electrocardiographic waveform measurement processing (S11), the contact detection electrode switching unit 93 switches the electrode to be connected to the first detection circuit 91 (S12). Thereafter, processing of inputting the physical condition (subjective symptom) of the user at the time of the electrocardiographic measurement is performed (S13), processing of inputting the exercise load of the user at the time of the electrocardiographic measurement is subsequently performed (S14), and the series of processing is terminated. Hereinafter, each processing of step S11 (electrocardiographic waveform measurement processing), step S13 (physical condition input processing), and step S14 (exercise load input processing) will be described in detail in order.

Electrocardiographic Measurement Processing

Figure 7:
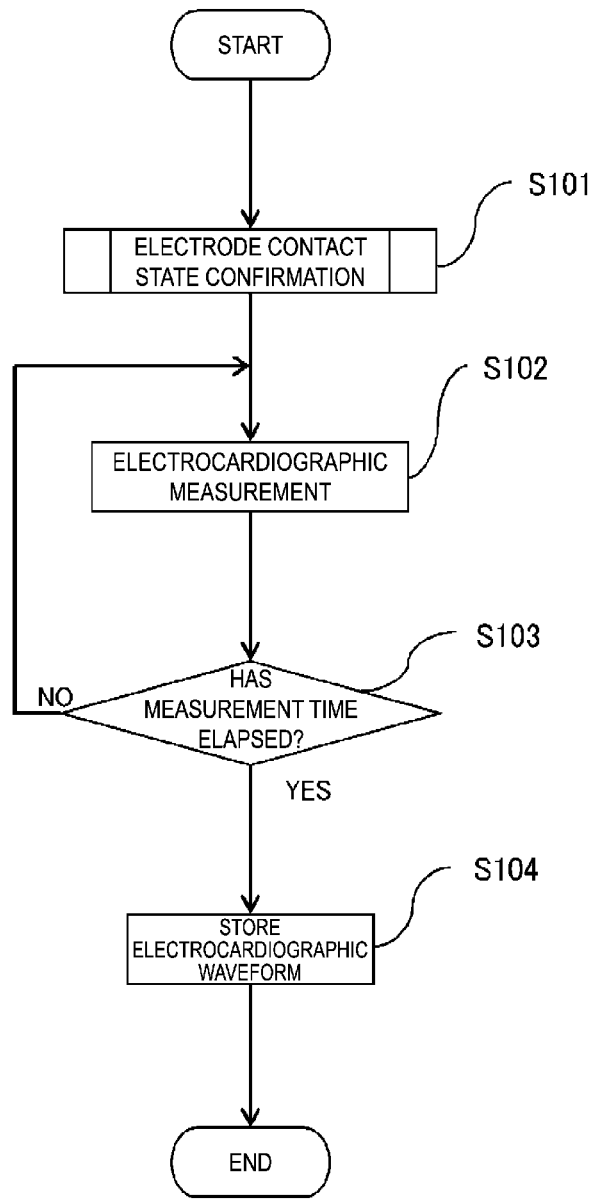
FIG. 7 is a flowchart illustrating a subroutine at the time of electrocardiographic waveform measurement of the portable electrocardiograph according to the first embodiment.
Figure 8:
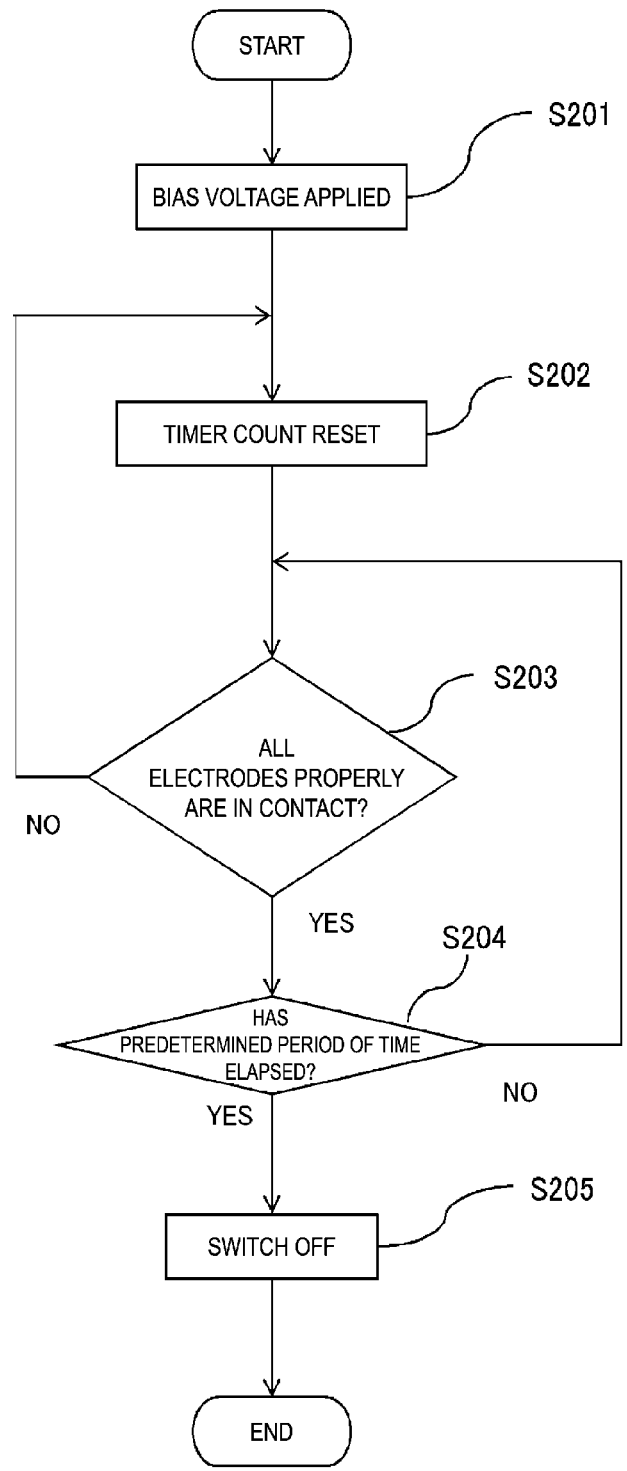
FIG. 8 is a flowchart illustrating a subroutine related to electrode contact detection processing before the electrocardiographic waveform measurement in the portable electrocardiograph according to the first embodiment.

With reference to FIG. 7, prior to electrocardiographic measurement, the user operates the power switch 16 to turn ON the power source of the portable electrocardiograph 1. Then, the user holds the portable electrocardiograph 1 with the right hand, with the right-hand index finger in contact with the first right electrode 12b and the second right electrode 12c, and with the left electrode 12a in contact with the skin at a location to be measured. Then, the control unit 101 detects the contact state of each of the electrodes via the electrode unit 12 and the contact state determination unit 110 (S101).

Here, the processing of the subroutine of step S101 will be described with reference to FIG. 8. First, when the power switch 16 is turned ON, the control unit 101 turns ON the first switching element 912 and the second switching element 922, and applies a bias voltage to the left electrode 12a and the second right electrode 12c (S201). Note that at this time, in the contact detection electrode switching unit 93, the first selector 931 connects the left electrode 12a to the first detection circuit 91, and the second selector 932 connects the first right electrode 12b to the ground.

Here, when all of the left electrode 12a, the first right electrode 12b, and the second right electrode 12c are in contact with the body, both the first comparator 910 and the second comparator 920 output "High", and the contact state determination unit 110 determines that all of the electrodes are in contact with the body. Then, if the "High" signal is continuously output for a predetermined period of time (for example, 3 seconds), it can be determined that each electrode is correctly brought into contact with the user and preparation for electrocardiographic measurement is completed. Here, whether or not the predetermined time has elapsed is required to be determined by referring to the timer unit 104. In step S202, the control unit 101 resets (sets to 0) a timer count value (hereinafter referred to as a contact time count value) for measuring time during which all the electrodes are in the contact state.

To be more specific, when the contact state determination unit 110 determines in step S203 that each of the left electrode 12a, the first right electrode 12b, and the second right electrode 12c is in contact with the body, the control unit 101 proceeds to step S204 and determines whether or not predetermined time has elapsed in that state. On the other hand, when it is determined in step S203 that all the electrodes are not correctly in contact with the body, the process returns to step S202, the contact time count value is reset, and the subsequent processing is repeated.

When it is determined in step S204 that the predetermined time has not elapsed, the control unit 101 returns to step S203 and the subsequent processing is repeated. On the other hand, when it is determined in step S204 that the predetermined time has elapsed, the first switching element 912 and the second switching element 922 are turned OFF to invalidate the pull-up resistor (step S205), and the subroutine is terminated.

Returning to the explanation of FIG. 7, after the subroutine of step S101 is terminated, the control unit 101 executes the actual electrocardiographic measurement processing (step S102), performs processing for determining whether or not the elapsed time of the electrocardiographic measurement has reached a predetermined measurement time (for example, 30 seconds) (step S103). Here, if it is determined that the predetermined amount of time has not elapsed, the process returns to step S102, and the subsequent processing is repeated. On the other hand, when it is determined that the predetermined measurement time has elapsed, the measurement is terminated and storage in the storage unit 105 (long-term storage medium) is performed (S104).

When the processing of the electrocardiographic waveform measurement is terminated, the user subsequently performs an operation of inputting (and recording) the physical condition and the exercise load at the time of the electrocardiographic measurement. For this reason, when the electrocardiographic measurement processing is terminated, the control unit 101 performs processing of switching the connection electrode to the first detection circuit 91 in the contact detection electrode switching unit 93 (S12). When the connection electrode to the first detection circuit 91 is switched from the left electrode 12a to the first right electrode 12b, the left electrode 12a becomes the ground electrode, and the first comparator 910 outputs a signal indicating whether or not the first right electrode 12b is in contact. Note that the switching processing may be automatically performed after a lapse of predetermined time from the end of the measurement, or may be performed by receiving input from the user, such as double tapping the power switch 16.

In the input phase of the physical condition and the exercise load at the time of electrocardiographic measurement after step S13, the user holds the portable electrocardiograph 1 in the mode illustrated in FIG. 2 and taps (i.e., comes in contact with) the first right electrode 12b and the second right electrode 12c to select and determine items corresponding to the respective types of processing. Specifically, by tapping only the second right electrode 12c, predetermined item feeding operation is performed, and by tapping only the first right electrode 12b, item return operation is performed. Furthermore, by tapping both the first right electrode 12b and the second right electrode 12c, operation of determining the selected item is performed. Further, other input operation may be enabled by tapping both the first right electrode 12b and the second right electrode 12c twice within predetermined time (so-called double tapping).

Physical Condition Information Input Processing

Figure 9:
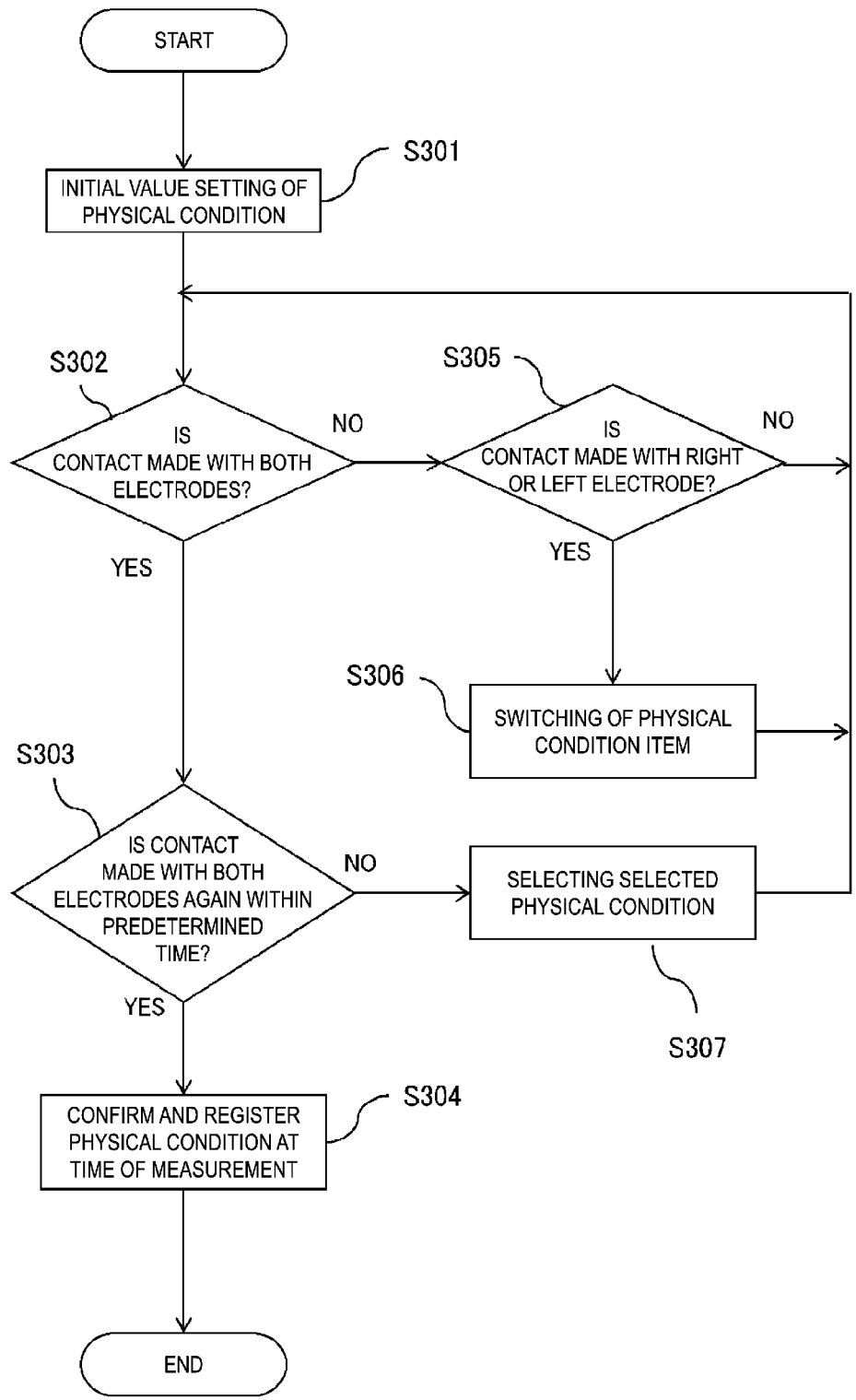
FIG. 9 is a first flowchart illustrating a subroutine related to processing after the electrocardiographic waveform measurement in the portable electrocardiograph according to the first embodiment.

Based on FIG. 9, a flow of processing for inputting the physical condition of the user at the time of electrocardiographic measurement (S13) will be described. First, the control unit 101 sets an item, which is defined as an initial value, among the items related to the physical condition (S301). For example, chest pain, dizziness, malaise, nausea, palpitations, shortness of breath, syncope, and others (no abnormality or the like) are defined as the items related to the physical condition, and for example, chest pain is set as an initial value.

Next, the control unit 101 causes the contact state determination unit 110 to determine whether or not the user simultaneously contacts both the first right electrode 12b and the second right electrode 12c (i.e., whether or not both the first comparator 910 and the second comparator 920 simultaneously output "High") (S302). Here, the process proceeds to step S303 when it is determined that the contact is made simultaneously on both electrodes.

On the other hand, if it is determined in step S302 that the user does not come into contact with both the first right electrode 12b and the second right electrode 12c simultaneously, the process proceeds to step S305, and processing of determining whether the contact is made with any of the first right electrode 12b and the second right electrode 12c is performed. Here, if it is determined that the user is not in contact with any of the electrodes, the process returns to step S302, and the subsequent processing is repeated. On the other hand, if it is determined in step S305 that the contact is made with either the first right electrode 12b or the second right electrode 12c, an item is fed or returned (item is switched) in accordance with the electrode in which the contact is made (S306), and the process returns to step S302, and the subsequent processing is repeated.

In step S303, processing of determining whether or not the user comes into contact with both the first right electrode 12b and the second right electrode 12c at the same time (that is, whether or not they are double-tapped) is performed again within predetermined time. If it is determined that the double tap has not been performed, the currently selected item is temporarily determined (S307), and the process returns to step S302, and the subsequent processing is repeated. That is, by repeating the processing from step S302 to step S307, a plurality of items can be registered. The reason for performing such processing is to record a plurality of items in accordance with a plurality of subjective symptoms (for example, palpitations and dizziness) assumed to be present in relation to the physical condition.

On the other hand, when it is determined in step S303 that both the first right electrode 12b and the second right electrode 12c have been double-tapped, the control unit 101 confirms all the currently set items as the physical condition of the user at the time of the electrocardiographic measurement and registers them in the storage unit 105 (step S304), and terminates the routine of step S13.

Exercise Load Information Input Processing

Figure 10:
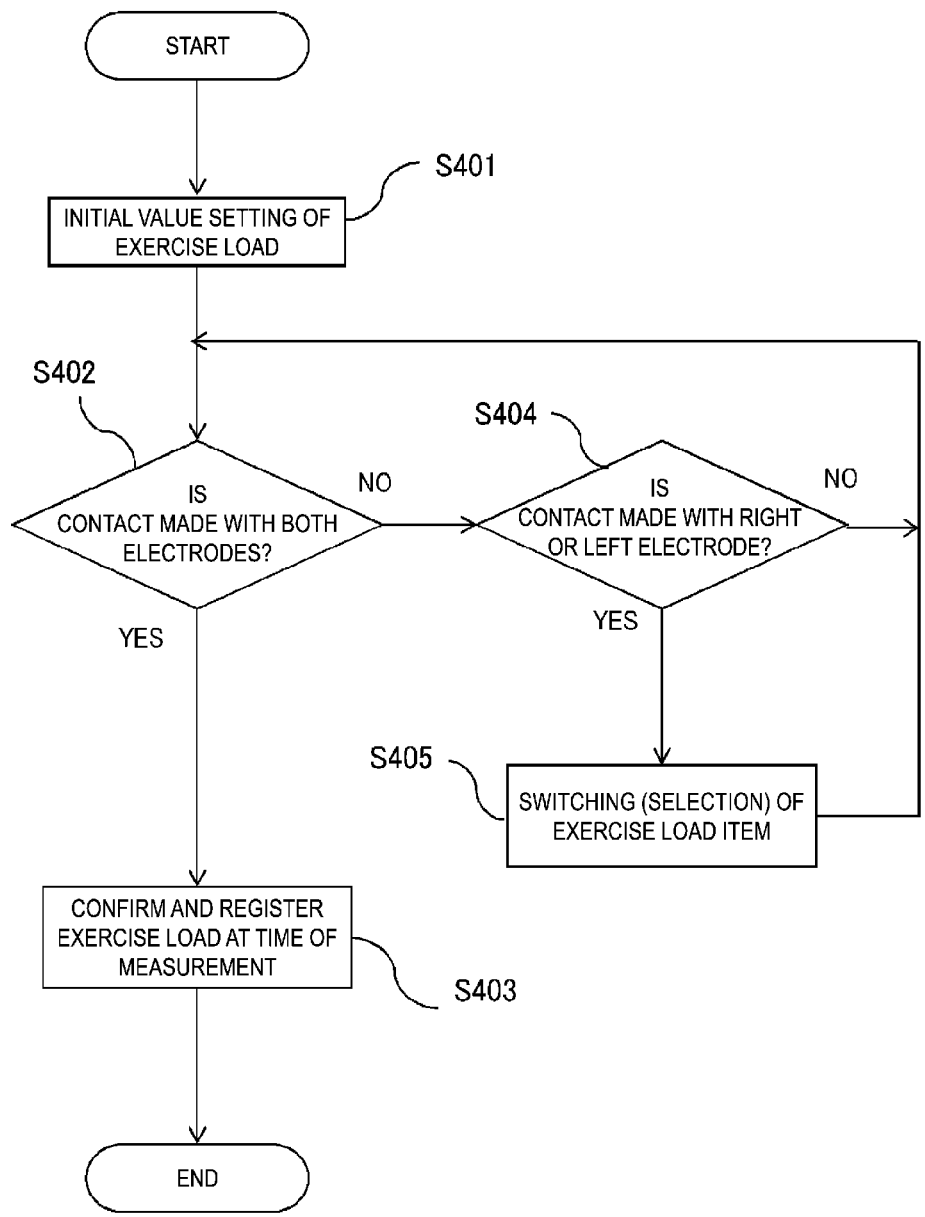
FIG. 10 is a second flowchart illustrating a subroutine related to processing after the electrocardiographic waveform measurement in the portable electrocardiograph according to the first embodiment.

Next, on the basis of FIG. 10, the flow of the processing for inputting the exercise load of the user at the time of electrocardiographic measurement (S14) is described. First, the control unit 101 sets an item, which is defined as an initial value, among the items related to the exercise load (S401). As the items related to the exercise load, for example, large, normal, small, and rest are defined, and for example, normal is set as an initial value.

Next, the control unit 101 causes the contact state determination unit 110 to determine whether or not the user simultaneously comes into contact with both the first right electrode 12b and the second right electrode 12c (i.e., whether or not both the first comparator 910 and the second comparator 920 simultaneously output "High") (S402).

Here, when it is determined that the user does not come into contact with both the first right electrode 12b and the second right electrode 12c simultaneously, the process proceeds to step S404, and processing of determining whether the contact is made with any of the first right electrode 12b and the second right electrode 12c is performed. Here, if it is determined that the user is not in contact with any of the electrodes, the process returns to step S402, and the subsequent processing is repeated.

On the other hand, if it is determined in step S404 that the contact is made with either the first right electrode 12b or the second right electrode 12c, an item is fed or returned (item is switched) in accordance with the electrode in which the contact is made (S405), and the process returns to step S402, and the subsequent processing is repeated.

On the other hand, when it is determined in step S402 that the user comes into contact with both electrodes of the first right electrode 12b and the second right electrode 12c simultaneously, the control unit 101 confirms the currently set item as the exercise load of the user at the time of electrocardiographic measurement and registers it in the storage unit 105 (step S403), and the routine of step S14 is terminated.

According to the portable electrocardiograph 1 of the present embodiment having the above-described configuration, even in a small-sized measurement device only including electrodes and a power source (and a power switch) for electrocardiographic measurement, desired information such as a physical condition and an exercise load at the time of electrocardiographic measurement can be input and stored together with measurement data. Note that in the present embodiment, the control unit 101 corresponds to the input receiver in the present invention.

Second Embodiment

Device Configuration

Next, a portable electrocardiograph 10 according to another embodiment of the present invention will be described with reference to FIG. 11 to FIG. 14. Since the portable electrocardiograph 10 according to the present embodiment has many configurations and functions in common with the portable electrocardiograph 1 described above, the same configurations, functions, and processing are denoted by the same reference signs and will not be described in detail.

Figure 11:
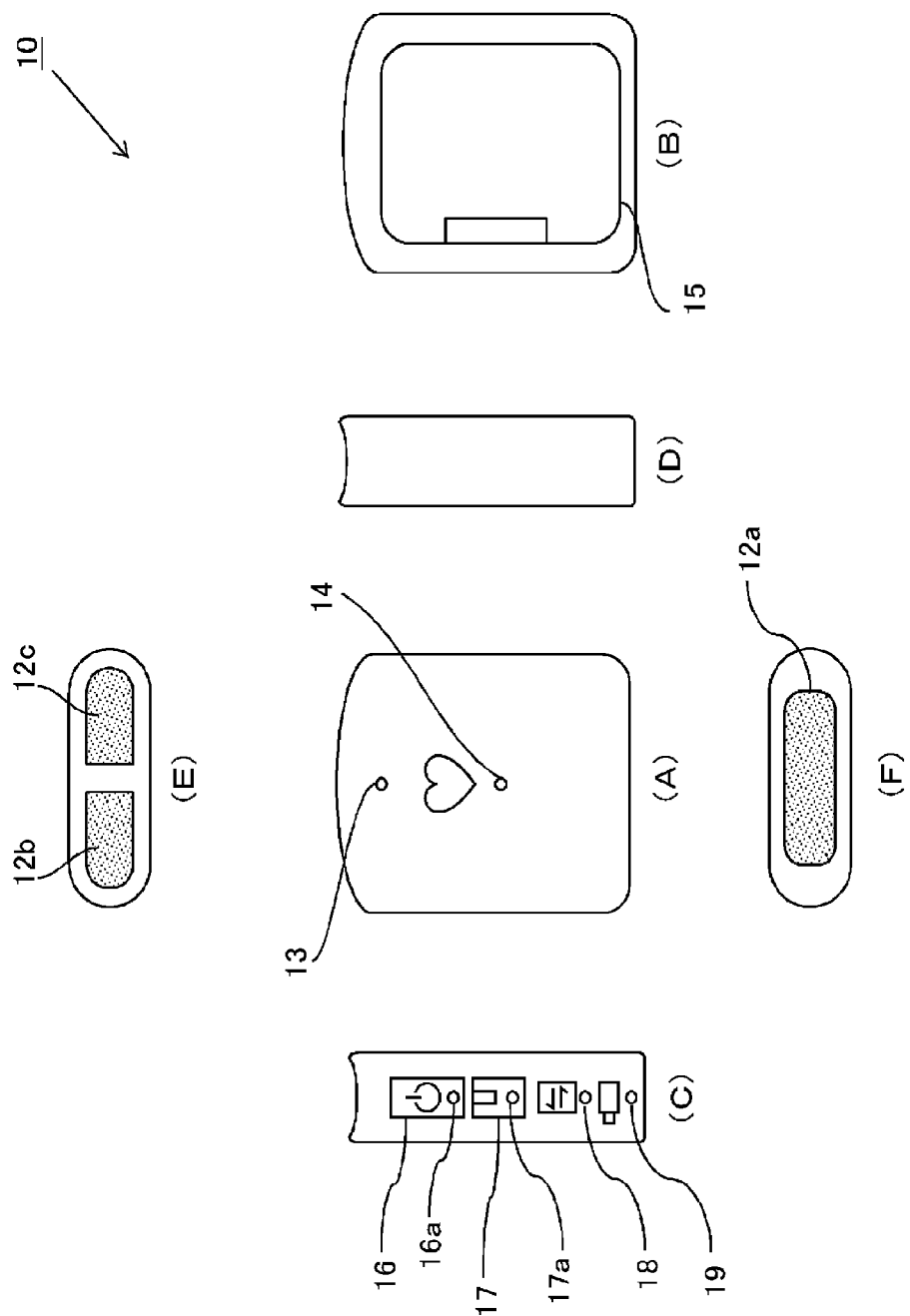
FIG. 11 is a six-sided view illustrating a configuration of a portable electrocardiograph according to a second embodiment. (A) of FIG. 11 is a front view illustrating the configuration of the portable electrocardiograph according to the second embodiment. (B) of FIG. 11 is a rear view illustrating the configuration of the portable electrocardiograph according to the second embodiment. (C) of FIG. 11 is a left side view illustrating the configuration of the portable electrocardiograph according to the second embodiment. (D) of FIG. 11 is a right side view illustrating the configuration of the portable electrocardiograph according to the second embodiment. (E) of FIG. 11 is a plan view illustrating the configuration of the portable electrocardiograph according to the second embodiment. (F) of FIG. 11 is a bottom view illustrating the configuration of the portable electrocardiograph according to the second embodiment.

FIG. 11 is a diagram illustrating a configuration of the portable electrocardiograph 10 according to the present embodiment. (A) of FIG. 11 is a front view illustrating the front of the body. Similarly, (B) of FIG. 11 is a rear view, (C) of FIG. 11 is a left side view, (D) of FIG. 11 is a right side view, (E) of FIG. 11 is a plan view, and (F) of FIG. 11 is a bottom view.

As illustrated in FIG. 11, in the portable electrocardiograph 10 according to the present embodiment, a left electrode 12a, a first right electrode 12b, and a second right electrode 12c are provided on a bottom surface and an upper surface, similarly to the portable electrocardiograph 1 according to the first embodiment.

In addition, various operation units and indicators are disposed on a left side surface of the portable electrocardiograph 10. Specifically, a power switch 16, a power LED 16a, a Bluetooth (registered trademark) Low Energy (BLE) communication button 17, a BLE communication LED 17a, a memory residual display LED 18, a battery exchange LED 19, and the like, are provided.

Additionally, a first LED notification unit 13 and a second LED notification unit 14 are provided at the front surface of the portable electrocardiograph 10, and a battery housing opening and a battery cover 15 are arranged at the rear surface of the portable electrocardiograph 10.

Figure 12:
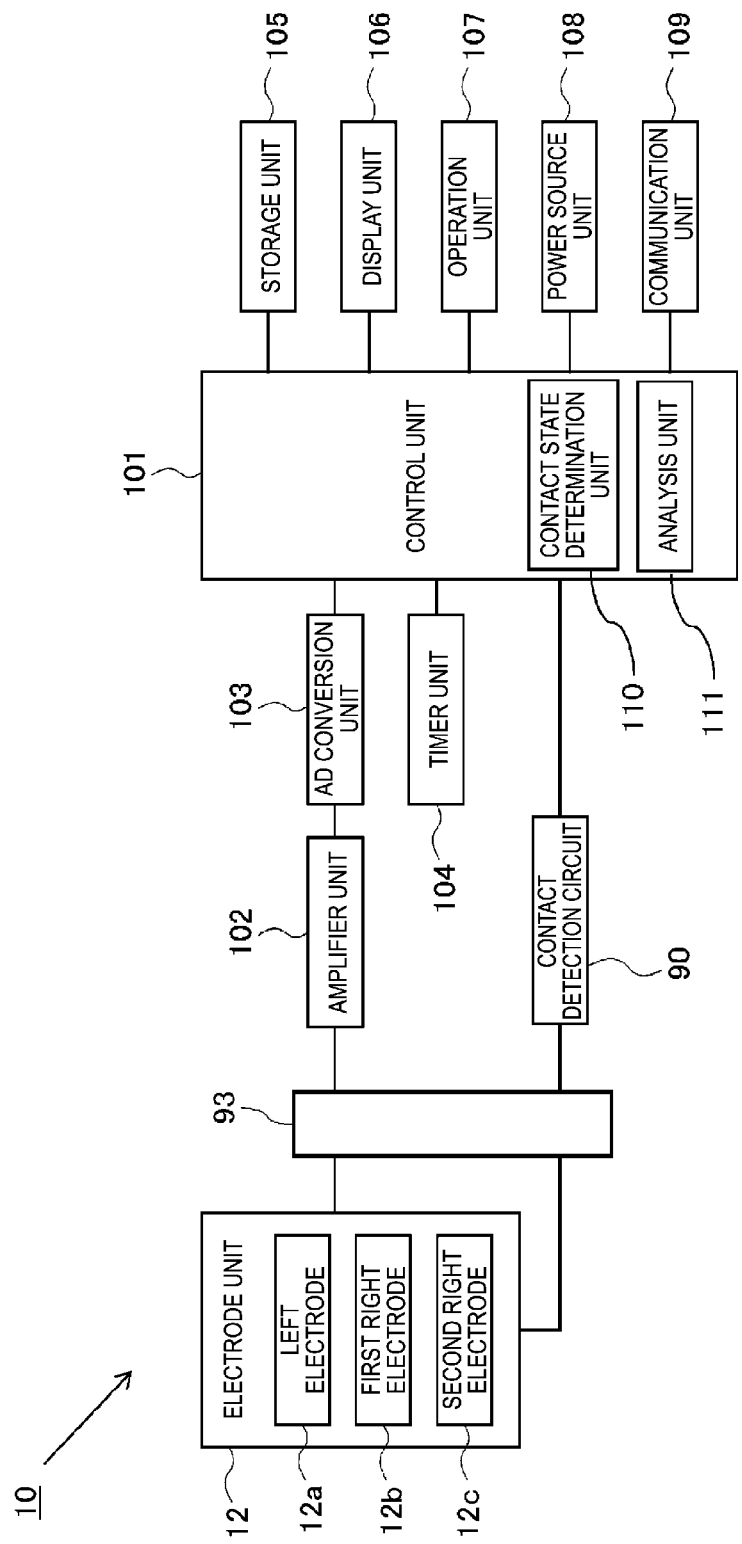
FIG. 12 is a block diagram illustrating a functional configuration of the portable electrocardiograph according to the second embodiment.

Also, in FIG. 12, a block diagram illustrating a functional configuration of the portable electrocardiograph 10 is described. As illustrated in FIG. 12, the portable electrocardiograph 10 includes functional units including a control unit 101, an electrode unit 12, an amplifier unit 102, an AD conversion unit 103, a timer unit 104, a storage unit 105, a display unit 106, an operation unit 107, a power source unit 108, a communication unit 109, a contact detection circuit 90, a contact state determination unit 110, and an analysis unit 111.

Although the basic configuration of the control unit 101 is similar to that of the portable electrocardiograph 1, the portable electrocardiograph 10 according to the present embodiment further includes a functional module of an analysis unit 111. The analysis unit 111 analyzes the measured electrocardiographic waveform for the presence of disturbance or the like, and outputs a result indicating whether or not the electrocardiographic waveform obtained at least during measurement is normal.

The display unit 106 includes the first LED notification unit 13, the second LED notification unit 14, the power LED 16a, the BLE communication LED 17a, the memory residual display LED 18, the battery exchange LED 19 and the like, and transmits various types of information to the user by turning on or blinking the LED. Note that, in the present embodiment, the display unit 106 (and the control unit 101) corresponds to the notifier of the present invention. Details of the display unit will be described later.

The communication unit 109 includes an antenna for wireless communication, and has a function of communicating with another device such as an information processing terminal by at least BLE communication. Additionally, a terminal may be provided for wired communication.

Since other configurations and functions of the portable electrocardiograph 10 are the same as those of the portable electrocardiograph 1 according to the first embodiment, description thereof will be omitted.

Flow of Processing by Portable Electrocardiograph

Figure 13:
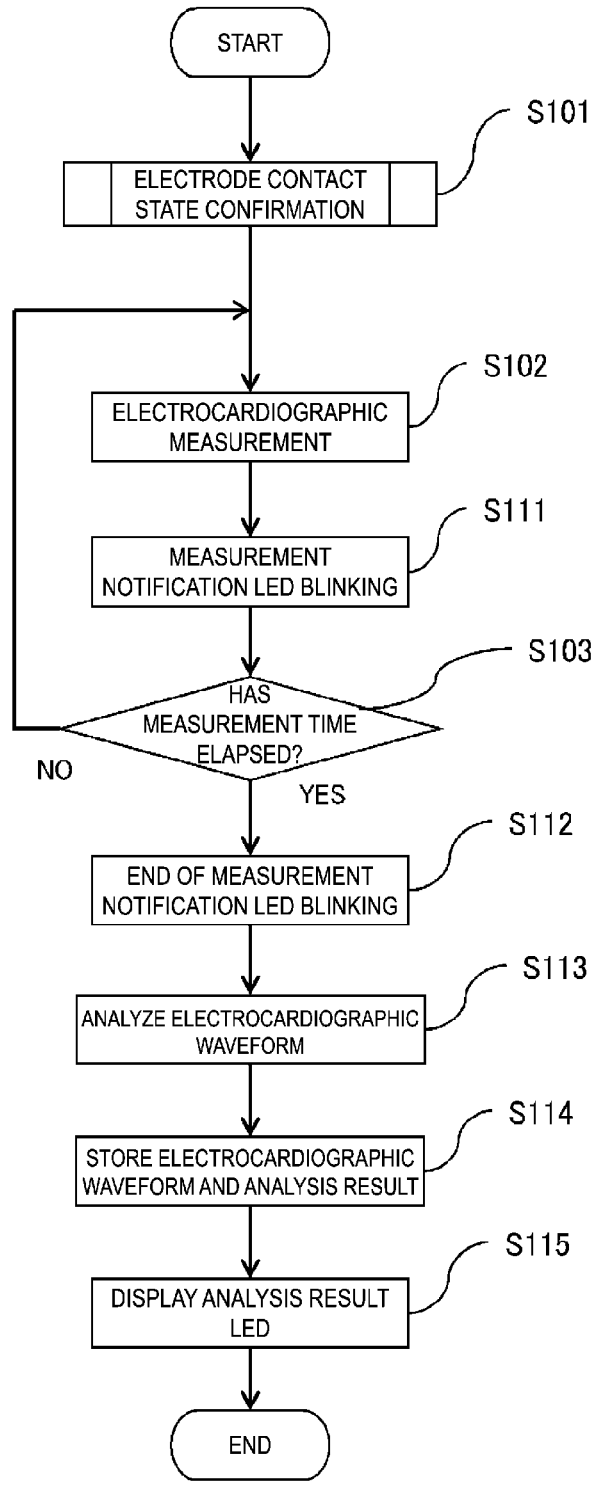
FIG. 13 is a flowchart illustrating a subroutine at the time of electrocardiographic waveform measurement in the portable electrocardiograph according to the second embodiment; and, FIG. 14(A) is a first explanatory diagram related to LED display of the portable electrocardiograph according to the second embodiment.

Next, a flow of processing of the portable electrocardiograph 10 when the electrocardiographic measurement is performed will be described. Note that, also in the present embodiment, after the electrocardiographic waveform measurement processing is performed, the electrode is switched by the contact detection electrode switching unit 93, and then the input operation of the physical condition information and the exercise load information (hereinafter collectively referred to as information input processing) is performed in the same manner. Hereinafter, the operation of the portable electrocardiograph 10 when the electrocardiographic measurement is performed will be described with reference to FIG. 13. FIG. 13 is a flowchart illustrating a subroutine at the time of electrocardiographic waveform measurement in the portable electrocardiograph 10 according to the present embodiment.

With reference to FIG. 13, prior to measurement, the user operates the power switch 16 to turn ON the power source of the portable electrocardiograph 10. As a result, the power LED 16a is turned on to indicate that the power source is ON. Then, the user holds the portable electrocardiograph 10 with the right hand, with the right-hand index finger in contact with the first right electrode 12b and the second right electrode 12c, and with the left electrode 12a in contact with the skin at a location to be measured. Then, the control unit 101 detects the contact state of each of the electrodes via the electrode unit 12 and the contact state determination unit 110 (S101). Note that the subroutine related to the contact state detection is the same as that of the first embodiment, and thus description thereof is omitted.

After the subroutine of step S101 is terminated, the control unit 101 executes the actual electrocardiographic measurement processing (step S102). While the electrocardiographic measurement is performed, the control unit 101 stores the measurement value in the storage unit 105 at any time, and displays that the electrocardiographic measurement is being performed by blinking the first LED notification unit 13 on the front surface of the body at a predetermined rhythm (S111).

Then, the control unit 101 performs processing for determining whether or not the elapsed time of the electrocardiographic measurement has reached a predetermined measurement time (for example, 30 seconds) (step S103). Here, if it is determined that the predetermined amount of time has not elapsed, the process returns to step S102, and the subsequent processing is repeated. On the other hand, if it is determined that the predetermined measurement time has elapsed, the measurement is completed, and processing of terminating the blink of the first LED notification unit 13 is performed (step S112).

Subsequently, the control unit 101 causes the analysis unit 111 to analyze the measurement data (electrocardiographic waveform) stored in the storage unit 105 (S113), and the analysis result is stored in the long-term storage medium together with the electrocardiographic waveform (S114). Then, the control unit 101 displays the result of the analysis by the second LED notification unit 14 (S115), and terminates the series of processing. Note that for the display of the analysis result, for example, the LED may be lighted only in a case where the electrocardiographic waveform is found abnormal or may be lighted in accordance with a lighting and blinking method corresponding to the analysis result.

Thereafter, information input processing is performed in the same manner, however, since the portable electrocardiograph 10 according to the present embodiment includes the display unit 106, the display unit 106 can be utilized when inputting the physical condition information and the exercise load information.

Figure 14A:
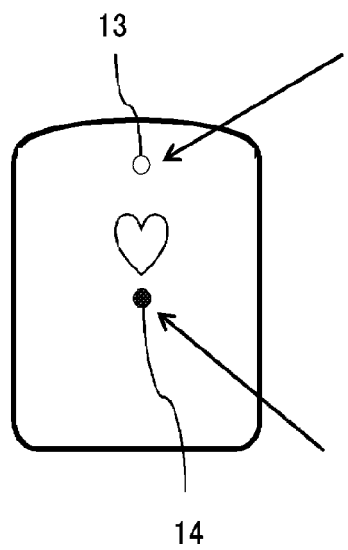
FIG. 14(B) is a second explanatory diagram related to LED display of the portable electrocardiograph according to the second embodiment.
Figure 14B:
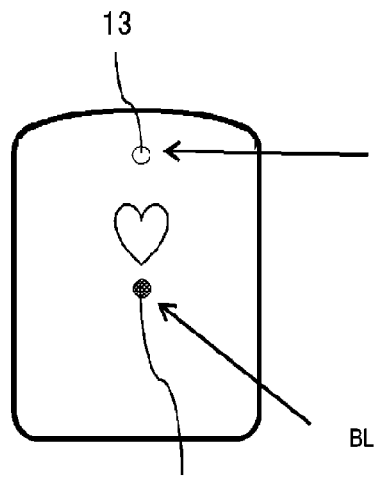

FIG. 14 is an explanatory diagram illustrating states of the first LED notification unit 13 and the second LED notification unit 14 when the information input processing is performed. FIG. 14(A) illustrates a display mode of the first LED notification unit 13 and the second LED notification unit 14 when the physical condition information is input, and FIG. 14(B) illustrates a display mode of the first LED notification unit 13 and the second LED notification unit 14 when the exercise load information is input.

The second LED notification unit 14 performs display indicating which of the physical condition information and the exercise load information is currently input in the phase, i.e., step S13 or step S14 in FIG. 6. To be specific, as illustrated in FIG. 14, the second LED notification unit 14 lights up in red in step S13, and lights up in blue in step S14.

The first LED notification unit 13 performs display for indicating which item is being selected by lighting in a color corresponding to the item related to the information currently being input. To be more specific, as illustrated in FIG. 14, in step S13, red lighting indicates that "chest pain" is being selected, and purple lighting indicates that "dizziness" is being selected. Similarly, in the case of step S14, red lighting indicates that the exercise load "Large" is being selected, and yellow lighting indicates that the exercise load "Normal" is being selected.

As specific processing, when the physical condition information is input, the control unit 101 sets the item of the initial value (for example, chest pain) in step S301 and turns on the first LED notification unit 13 in a color (for example, red) corresponding to the item. Then, in step S306, processing of switching the item is performed, and the lighting color is switched to a color (purple) corresponding to the switched item (for example, dizziness). It is sufficient if the same processing is performed when the exercise load information is input.

According to the portable electrocardiograph 10 having such a configuration, it is possible to perform various types of display by the LED which does not occupy a large space, and even when input operation using the electrode is performed, the user can perform input after confirming an item to be currently input. This makes it possible to greatly improve the convenience at the time of input operation.

Other Points

The description of the embodiments described above is merely illustrative of the present invention, and the present invention is not limited to the specific embodiments described above. Within the scope of the technical idea of the present invention, various modifications and combinations may be made.

For example, in each of the above-described embodiments, processing of switching the determination content of the contact state determination unit 110 may be performed together with the processing of switching the connection electrode in step S12. That is, in step S101, the contact state determination unit 110 performs processing of determining only whether or not all the electrodes are in the contact state and outputting the determination result. On the other hand, at the time of inputting the physical condition and the exercise load at the time of electrocardiographic measurement after the subsequent step S13, the contact state determination unit 110 may individually determine and output the contact states of the first right electrode 12b and the second right electrode 12c. In this manner, the contact determination of the electrode can be properly used depending on the case of performing the measurement of the biological information and the case of performing the input of the information, so that it is possible to prevent the input of the information from being erroneously performed at the time of the measurement of the biological information from occurring, and vice versa.

Additionally, in each of the above-described embodiments, the processing of step S13 and step S14 (information input processing) is performed after the measurement of the electrocardiographic waveform. However, the processing is not necessarily limited to such a flow, and the information input processing may be performed before the measurement of the electrocardiographic waveform. Furthermore, the sequence of the processing in step S13 and step S14 may be reversed.

Further, although the second embodiment has the configuration in which the LED is provided as the notifier, the notifier is not limited to the LED, and notification may be performed by display on a liquid crystal display or the like or sound output from a speaker.

Although not described in detail in the above embodiment, the electrocardiograph and another information terminal device such as a smartphone can be used in cooperation with each other by the BLE communication function of the communication unit 109. Although the present invention is applied to a portable electrocardiograph in the above embodiment, the present invention can also be applied to other biological measurement devices such as a body composition meter.

REFERENCE SIGNS LIST

10 Portable electrocardiograph
12a Left electrode
12b First right electrode
12c Second right electrode
13 First LED notification unit
14 Second LED notification unit
15 Battery cover
16 Power switch
16a Power LED
17 Communication button
17a BLE Communication LED
18 Memory residual display LED
19 Battery change LED
91 First detection unit
910 First comparator
911 First bias power source
912 First switching element 913 First pull-up resistor
914 First RC filter
915 First reference voltage power source
916a First reference voltage resistor
916b First reference voltage resistor
917a First hysteresis resistor
917b First hysteresis resistor
92 Second detection unit
920 Second comparator
921 Second bias power source
922 Second switching element
923 Second pull-up resistor
924 Second RC filter
925 Second reference voltage power source
926a Second reference voltage resistor
926b Second reference voltage resistor
927a Second hysteresis resistor
927b Second hysteresis resistor
93 Contact detection electrode switching unit
931 First selector
932 Second Selector
94 Differential amplifier

What is claimed is:

1. A biological information measurement device including a first electrode, a second electrode, and a third electrode, the biological information measurement device measuring biological information of a measurement target based on a potential difference between the first electrode and the third electrode, the biological information measurement device comprising:
an electrode contact state detector including a first contact detection circuit connected to either the first electrode or the second electrode among the electrodes, a second contact detection circuit connected to the third electrode, and
a processor configured to determine a contact state indicating which of the electrodes is in contact with a surface of the measurement target based on a first signal output from the first contact detection circuit and a second signal output from the second contact detection circuit,
the processor further configured to receive a contact of each of the electrodes with respect to the surface of the measurement target as input of predetermined operation associated with the contact state, and
a contact detection electrode switcher configured to switch an electrode connected to the first contact detection circuit between the first electrode and the second electrode.

2. The biological information measurement device according to claim 1, wherein
the contact detection electrode switcher connects one of the first electrode and the second electrode, which is not connected to the first contact detection circuit, to a ground.

3. The biological information measurement device according to claim 2, wherein
the processor is further configured to switch and execute, depending on the electrode connected to the first contact detection circuit, the determination of the contact state between a determination at time of measurement when the biological information of the measurement target is measured and a determination at time of operation input when the input of the predetermined operation is received; and,
the input receiver receives a contact of each of the electrodes with respect to the surface of the measurement target as the input of the predetermined operation associated with the contact state when the processor is executing the determination at the time of operation input.

4. The biological information measurement device according to claim 3, wherein:
the predetermined operation corresponding to the contact state includes
selecting at least a predetermined item.

5. The biological information measurement device according to claim 2, wherein
the predetermined operation corresponding to the contact state includes:
selecting at least a predetermined item.

6. The biological information measurement device according to claim 5, wherein:
the predetermined item includes
a physical condition or an exercise load state when the biological information of the measurement target is measured.

7. The biological information measurement device according to claim 1, wherein
the processor is further configured to switch and execute, depending on the electrode connected to the first contact detection circuit, the determination of the contact state between a determination at time of measurement when the biological information of the measurement target is measured and a determination at time of operation input when the input of the predetermined operation is received; and,
the input receiver receives a contact of each of the electrodes with respect to the surface of the measurement target as the input of the predetermined operation associated with the contact state when the processor is executing the determination at the time of operation input.

8. The biological information measurement device according to claim 7, wherein
the predetermined operation corresponding to the contact state includes:
selecting at least a predetermined item.

9. The biological information measurement device according to claim 8, wherein:
the predetermined item includes
a physical condition or an exercise load state when the biological information of the measurement target is measured.

10. The biological information measurement device according to claim 1, wherein
the predetermined operation corresponding to the contact state includes:
selecting at least a predetermined item.

11. The biological information measurement device according to claim 10, wherein
the predetermined item includes:
a physical condition or an exercise load state when the biological information of the measurement target is measured.

12. The biological information measurement device according to claim 10, wherein the processor is further configured to:
notify information related to measurement of the biological information when the biological information of the measurement target is measured, and notify information related to a content of the predetermined item when the input of the predetermined operation is received.

13. The biological information measurement device according to claim 1, wherein
the biological information is an electrocardiographic waveform.

14. The biological information measurement device according to claim 1, wherein
the processor is further configured to switch and execute, depending on the electrode connected to the first contact detection circuit, the determination of the contact state between a determination at time of measurement when the biological information of the measurement target is measured and a determination at time of operation input when the input of the predetermined operation is received; and,
the input receiver receives a contact of each of the electrodes with respect to the surface of the measurement target as the input of the predetermined operation associated with the contact state when the processor is executing the determination at the time of operation input.

15. The biological information measurement device according to claim 14, wherein:
the predetermined operation corresponding to the contact state includes selecting at least a predetermined item.

16. The biological information measurement device according to claim 1, wherein:
the predetermined item includes
a physical condition or an exercise load state when the biological information of the measurement target is measured.

* * * * *